US011493451B2

(12) United States Patent
Iftime et al.

(10) Patent No.: US 11,493,451 B2
(45) Date of Patent: Nov. 8, 2022

(54) COLORIMETRIC DRUG TEST STRIP USING POROUS SUPPORT MATERIAL

(71) Applicant: Palo Alto Research Center Incorporated, Palo Alto, CA (US)

(72) Inventors: Gabriel Iftime, Dublin, CA (US); Stephen Matthew Meckler, Mountain View, CA (US); David Eric Schwartz, Concord, MA (US); Joerg Martini, San Francisco, CA (US); Jessica Louis Baker Rivest, Palo Alto, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 199 days.

(21) Appl. No.: 16/724,644

(22) Filed: Dec. 23, 2019

(65) Prior Publication Data
US 2021/0190697 A1 Jun. 24, 2021

(51) Int. Cl.
*B01L 3/00* (2006.01)
*G01N 21/78* (2006.01)
*G01N 33/94* (2006.01)

(52) U.S. Cl.
CPC ............ *G01N 21/78* (2013.01); *B01L 3/5023* (2013.01); *B01L 3/502715* (2013.01); *G01N 33/946* (2013.01); *B01L 2300/0825* (2013.01)

(58) Field of Classification Search
CPC .......... B01L 3/5023; B01L 3/502; B01L 3/50; B01L 3/502715; B01L 2300/0825; G01N 21/78; G01N 21/77; G01N 21/75; G01N 33/946; G01N 33/94; G01N 33/50; G01N 33/48

USPC ......................................................... 422/42
See application file for complete search history.

(56) References Cited

U.S. PATENT DOCUMENTS

| 7,897,057 B1* | 3/2011 | O'Connor ............... C03C 15/00 216/24 |
| 9,360,398 B2 | 6/2016 | Gold et al. |
| 2009/0053832 A1 | 2/2009 | Link et al. |
| 2016/0077091 A1 | 3/2016 | Tyrrell et al. |
| 2016/0167042 A1* | 6/2016 | Tyrrell .................. B01L 3/5023 422/402 |

(Continued)

FOREIGN PATENT DOCUMENTS

| EP | 3502670 | 6/2019 |
| GB | 2404023 | 1/2005 |
| WO | 2009026074 | 2/2009 |

OTHER PUBLICATIONS

Bell et al., "A Microfluidic Device for Presumptive Testing of Controlled Substances", J. Forensic Sci, 52 (4), Jul. 2007, pp. 884-888.

(Continued)

*Primary Examiner* — Christine T Mui
(74) *Attorney, Agent, or Firm* — Mueting Raasch Group

(57) ABSTRACT

A test strip includes a substantially transparent substrate and one or more colorimetric test spots on the transparent substrate. Each colorimetric test spot has one or more sensing chemicals chemically attached onto a porous support material. The porous support material has at least one exposed surface configured to absorb a body fluid. The one or more sensing chemicals are configured to change a color in response to a presence of a target drug in the body fluid.

28 Claims, 5 Drawing Sheets

(56) References Cited

U.S. PATENT DOCUMENTS

2019/0187062 A1* 6/2019 Iftime ............... G01N 21/78

OTHER PUBLICATIONS

Desrosiers et al., "Oral Fluid and Plasma 3,4-Methylenedioxymethamphetamine (MDMA) and Metabolite Correlation after Controlled Oral MDMA Administration", Anal Bioanal Chem. 2013, 405(12), 4067-4076.
Fabritius et al., "Comparison of cannabinoid concentrations in oral fluid and whole blood between occasional and regular cannabis smokers prior to and after smoking a cannabis joint", Anal Bioanal Chem 2013, 405, 9791-9803.
Goledzinowski, "Pharmacokinetics and Detection of THC Impairment Traffic Safety Considerations in Canada", CCMTA/CCATM Annual Meeting, Jun. 4-7, 2017, 35 pages.
Huestis et al., "Methamphetamine Disposition in Oral Fluid, Plasma, and Urine", Ann N Y Acad Sci., 2007, 1098, 104 121.
Musile et al.,"The development of paper microfluidic devices for presumptive drug detection", Anal. Methods, 7, 2015, pp. 8025-8033.
Scheidweiler et al., "Pharmacokinetics of Cocaine and Metabolites in Human Oral Fluid and Correlation with Plasma Concentrations following Controlled Administration", Ther Drug Monit. 2010, 32(5): 628-637.
European Extended Search Report for EP Application No. 20212026.7 dated May 27, 2021, 8 pages.

* cited by examiner

COLORIMETRIC DRUG TEST STRIP USING POROUS SUPPORT MATERIAL

SUMMARY

The present disclosure is directed to a colorimetric test strip using porous support material. In one embodiment a test strip includes a substantially transparent substrate and one or more colorimetric test spots on the transparent substrate. Each colorimetric test spot has one or more sensing chemicals chemically attached onto a porous support material. The porous support material has at least one exposed surface configured to absorb a body fluid. The one or more sensing chemicals are configured to change a color in response to a presence of a target drug in the body fluid.

In another embodiment, a method involves collecting a sample of body fluid with an absorbent swab. The swab is placed with the collected sample into a test chamber of a test apparatus. Contact between the swab and a test strip is caused in the test chamber. The test strip includes one or more colorimetric test spots that are placed onto a transparent substrate or are embedded within a porous support material. The colorimetric test spots are illuminated and a wavelength emitted therefrom for first and second readings are detected. The first reading occurs just before or after the contact between the swab and the test strip and the second reading occurs a predetermined time after the contact. Based on a difference between the first and second readings that indicates a color change of the colorimetric test spot, a numeric value is determined for a concentration of a drug that is correlated with the color change. An indication of the numeric value is provided via the test apparatus.

In another embodiment, a system includes a test strip with a one or more colorimetric test spots that each include one or more sensing chemicals chemically attached onto a porous support. The system includes a swab operable to collect a sample of body fluid and a test apparatus. The test apparatus includes a test chamber comprising an optical reader and configured to receive the test strip and at least part of the swab. The test apparatus also includes an indicator device and a processor coupled to the optical reader and the indicator device. The processor is configured to: detect a wavelength of light emitted from the colorimetric test spot for first and second readings, the first reading occurring just before or after the contact between the swab and the test strip and the second reading occurring a predetermined time after the contact; based on a difference between the first and second readings that indicates a color change of the colorimetric test spot, determine a numeric value for a concentration of a drug that is correlated with the color change; and provide an indication of the numeric value via the indicator device.

These and other features and aspects of various embodiments may be understood in view of the following detailed discussion and accompanying drawings.

BRIEF DESCRIPTION OF THE DRAWINGS

The discussion below makes reference to the following figures, wherein the same reference number may be used to identify the similar/same component in multiple figures.

DETAILED DESCRIPTION

Figure 1A:
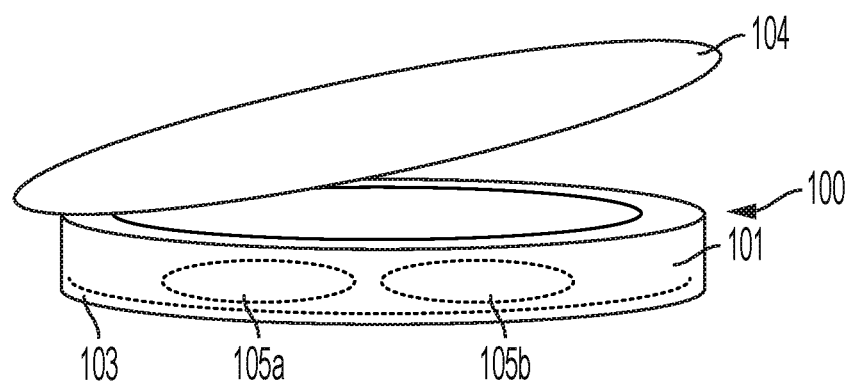
FIG. 1A is a diagram of a test strip according to an example embodiment.

The present disclosure is generally related to drug testing. There are known hazards with individuals performing operations such driving and operating machinery while under the influence of drugs and/or alcohol. For entities such as law enforcement or employers, there is a demand for a simple and expensive test for the presence of intoxicants in a person's system. Simple and inexpensive tests currently exist for the presence of alcohol in a person's system, but such is not necessarily the case for commonly used performance-affecting drugs such as marijuana, methamphetamines, and opioids.

In one region, for example, police set up roadside drug and alcohol testing on a random basis. Of all tests performed, approximately 1 in 170 drivers were over the legal limit with alcohol, but for drug testing, approximately 1 in 11 drivers revealed a positive test. It is believed that an increase in the amount of roadside drug testing will more effectively discourage drug driving. Unfortunately, it is currently difficult to significantly scale up testing for drugs. One reason is the cost of the testing. The current test costs $24 USD each, and if a positive test is detected, then a second test must be done that is then sent to the lab for evidentiary testing. This second test costs upwards of $500 USD and takes considerable time to get the results back from the lab.

Another reason preventing wider adoption of these drug tests is the time required for each test. The current roadside drug test takes up to 3 minutes to return a result after sample collection. The roadside tests also produce an unacceptable amount of false positive tests, close to 2%. These tests also require operation in limited conditions (e.g., ambient temperature) and can be somewhat difficult to perform in a roadside environment, e.g., holding the test the right way and consistently performing the correct sequence of operations.

Commercially available roadside drug tests include immunoassays, which has some disadvantages. For example, the screening test is relatively slow, the per-test cost is relatively high, detection error rates are relatively high, and the tests are relatively complicated to administer. In existing products, there are a limited number of detectable drug targets. Another type of proposed test uses colorimetrics with microfluidics (see Bell S C et al., J Forensic Sci. 2007 Jul; 52(4): 884-8; G. Musile et al., Anal. Methods, 2015, 7, 8025-8033). Disadvantages of this approach include an increased test duration due to the time it takes the solution to migrate through the channels to reach the test spots. Also, the advancement of the solvent front disturbs the sensing dyes, which result in poor colorability and reproducibility. Colorimetric test kits, which are often used in the workplace, include multiple flasks of solutions (often dangerous), are slow; and are not practical for use by the police for field test.

Development of reliable roadside drug testing faces significant challenges when compared with alcohol testing.

Unlike with alcohol, for example, there is much less clear correlation between the drug levels in blood or saliva and impairment. This is because the metabolism of drugs like tetrahydrocannabinol (THC), methamphetamine (MA) and cocaine is much more complex than that of ethanol. In addition, habitual users have elevated levels of drugs in their system even if they did not consume recently and may result in false positives for driving under the influence (DUI). These concentrations may be illegal for example in the workplace but may not necessarily produce impairment while driving.

Testing is further complicated by the fact that the time to peak effect and the maximum concentration of the drugs in the saliva change depending on the mode of administration. For example, smoked or vaped THC reaches the time to peak effect and maximum concentration in seconds or minutes, followed by rapid decay (1-2 hours). On the other hand, the THC concentration in saliva after being ingested from food, is about ten times lower than that of the same amount of smoked THC in the first 15 minutes and decreases slowly in about 24 hours after consumption.

The goal of roadside testing is to identify drivers whom are actively impaired while caught driving after drug consumption. In other words, the objective is to detect recent consumption instead of the residual amount of drug that may be present in body long after consumption at levels that do not create impairment, and which are below the police specified limits of detection.

While pharmacokinetic profile is specific to each individual drug, there are multiple challenges with immunoassay-based roadside drug testing. Current hand-held immunoassays drug testing devices from saliva detect the metabolites of the drugs in question. One challenge with metabolite testing is that depending on the drug and on the mode of administration, there may be delays in the detectability of the drug from the time of ingestion to the test time. For example, in the case of methylenedioxy-methamphetamine (MDMA) detection, the time to maximum concentration of (tmax) of MDMA is 2.8 hours, while for its main metabolite, methylenedioxyamphetamine (MDA), the tmax increases to 4.8 hours. Another challenge with some drugs is that the concentration of metabolites is orders or magnitude lower than that of the parent compound in the oral fluid (note that in this disclosure, the terms "parent compound," "parent," and "parent molecule" are used interchangeably). For example, in one study the THC concentration in saliva was measured to be ~2000× higher than that of the main metabolite, THC—COOH. This makes metabolite detection very challenging. Table 1 below shows the maximum concentration of the parent drugs and of the main metabolites for the three drugs (plus cocaine) which are considered in this disclosure, in blood and in oral fluid.

TABLE 1

| Drug | | Concentration in Saliva [ng/mL] | Cmax in blood or plasma [ng/mL] | Ratio Saliva/ Blood |
|---|---|---|---|---|
| THC (40 mg) [#] | Parent compound (THC) | 636 | 87 | 7.3 |
| | Metabolite (THC-COOH) | 0.3 | 41 | 0.007 |
| | Ratio Parent: Metabolite | 2120 | 2.1 | |
| MA (20 mg) [$] | Parent compound (MA) | 192 | 32 | 6 |
| | Metabolite (A) | 14 | 6 | 2.3 |
| | Ratio Parent: Metabolite | 13.7 | 5.3 | |

TABLE 1-continued

| Drug | | Concentration in Saliva [ng/mL] | Cmax in blood or plasma [ng/mL] | Ratio Saliva/ Blood |
|---|---|---|---|---|
| MDMA (75 mg)* | Parent compound (MDMA) | 1643 | 150 | 11 |
| | Metabolite (MDA) | 41 | 7 | 5.8 |
| | Ratio Parent: Metabolite | 40 | | |
| Cocaine (75 mg subcutaneous)** | Parent Compound (Cocaine) | 1092 | 305 | 3.6 |
| | Metabolite (BE + EME) | 265 | 371 | 0.7 |
| | Ratio Parent: Metabolite | 4.1 | 0.8 | |

[#] M. Fabritius et al., Comparison of cannabinoid concentrations in oral fluid and whole blood between occasional and regular cannabis smokers prior to and after smoking a cannabis joint, Anal Bioanal Chem 2013, 405, 9791-9803
[$] M. A. Huestis et al., Methamphetamine Disposition in Oral Fluid, Plasma, and Urine, Ann N Y Acad Sci., 2007, 1098, 104-121
*N. A. Desrosiers et al., Oral Fluid and Plasma 3,4-Methylenedioxymethamphetamine (MDMA) and Metabolite Correlation after Controlled Oral MDMA Administration, Anal Bioanal Chem. 2013, 405(12), 4067-4076
** K. B. Scheidweiler et al., Pharmacokinetics of Cocaine and Metabolites in Human Oral Fluid and Correlation with Plasma Concentrations following Controlled Administration, Ther Drug Monit. 2010, 32(5): 628-637.

Embodiments described below include test strips for detecting illicit drugs from body fluids. The test strips include a porous material supporting one or more colorimetric test spots. The test spots include one or more sensing chemicals of which at least one is chemically attached onto the porous support material. The presence of a target molecule is indicated by a color change in the test spot. An optical reader can be used to provide a numeric value for the concentration of the tested drugs.

When compared with existing drug detection methods from body fluids, e.g., saliva, the test strip described herein can provide results faster. The test is enabled by direct contact between the saliva from the collection swab and the test spots from the test strip. This eliminates the microfluidic or the chromatographic channels found in microfluidic test devices or in immunoassays.

The test strips described herein can have increased accuracy because the strips detect the parent compound instead of their metabolites. The concentration of the parent compound in saliva is always higher that of their metabolites. Colorimetric sensing dyes are attached to the porous support material (unlike other colorimetric sensors) which prevents dye leaching during contact with saliva sample. While embodiments may describe roadside drug testing from saliva, other bodily fluids may be used. Also, while testing scenarios describe human testing, such strips may be used to detect drugs in animals, e.g., detection of performance-enhancing drugs in racing animals.

Figure 1B:
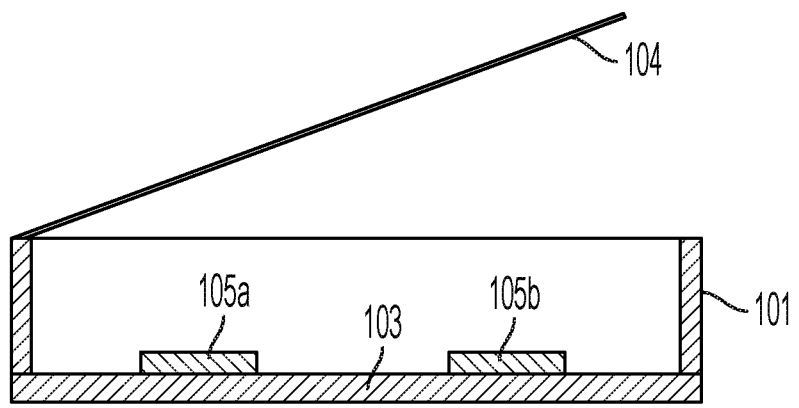
FIG. 1B is a cross section of the test strip according to an example embodiment.

In FIG. 1A, a diagram shows a test strip 100 according to an example embodiment. The test strip 100 includes an enclosure 101 in which one or more test spots 105*a*, 105*b*, are placed onto a substrate 103. Generally, at least the substrate material 103 is transparent at a wavelength of interest, e.g., in the visible light spectrum. The enclosure 101 is covered prior to use by a removable seal 104. Both the enclosure 101 and seal 104 are generally impermeable to gases and liquids, e.g., air, water, so as to protect the support material and sensing chemicals. FIG. 1B shows a cross-section the test strip.

In one embodiment, each individual test spot 105*a*, 105*b* includes a multitude of particles incorporating one or more sensing chemicals embedded within the porous support material. In another embodiment, each individual test spot includes a block incorporating one or more sensing chemicals embedded within the porous support material. Either the multitude of particles or the block structures are bonded to a substrate 103.

In another embodiment, the substrate 103 is part of the porous support material. In other words, the substrate 103 and the support materials are the same. In such a case, the substrate 103 contains multiple test spots within it, surrounded by porous substrate without sensing chemicals. The test spots can be fabricated placing drops of suitable sensing chemicals onto a flat surface of the porous material.

The porous support material may include an aerogel. In order to enable a high detected signal, the porous support material should be substantially transparent and colorless, so that the color of all the sensing chemicals both before and their new color after interaction with the tested analyte is available for detection. A poorly transparent or non-transparent support material will hide the sensing chemicals placed into the depth of the support material. The ideal porous support material is fully transparent to the wavelengths used for illumination and for detection of the color change. However, materials with a certain degree of transparency that is less than 100% are also suitable. For example, porous support materials with a transparency of 50% or 70% may be suitable but will be somewhat disadvantaged because the signal may be decreased.

At least one of the sensing chemicals is chemically bonded onto the walls of the pores of the porous support material in each test spot 105a, 105b, because it prevents leaching of the sensing chemical during contact with the test fluid sample. In one embodiment, chemical attachment of the sensing chemicals onto the porous support material achieved by grafting of the sensing chemicals onto the walls of a premade porous support materials, generally by chemical reaction between compatible functional groups present on both the sensing chemicals and the porous substrate.

The aerogel support material may be selected from a group including silica and polymer aerogels. Silica aerogels are typically made by the reaction of a silicon alkoxide with water in a solvent such as ethanol or acetone to form a gel. The reaction involves the presence of basic, acidic, or a fluoride-containing catalyst. The gel is generally purified by extraction with solvents such as ethanol and then is dried, typically by using supercritical $CO_2$. Generally, silica aerogels are relatively fragile and have some degree of haze. With respect to the porous support, silica aerogels usually contain unreacted silanol (Si—OH) groups on the surface of their skeletons, which can be used for bonding the sensing chemical.

Polymer aerogels are also suitable. Most of the known polymer aerogels are either colored or non-transparent because of haze. In order to be usable as support materials for the present invention, they should be substantially transparent and colorless. For a polymer aerogel to be substantially transparent, it requires that the size of its pore to be very small, typically the average pore size should be <20 nm. One preferred method for fabrication of polymer aerogels is radical polymerization of acrylate of vinyl monomers and crosslinkers, initiated by radical initiators. Traditional radical polymerization initiated by radical initiators such as benzoyl peroxide shows poor chain length control, that may result in aerogels with sub-optimal pore size control, e.g., large width of the pore size distribution, therefore large haze.

Methods for producing substantially transparent polymer aerogels have been disclosed recently in publications. These methods produce uniform and small pores by controlled living polymerization, wherein the polymer chain growth and therefore of the pore size, is mediated by a control agent. In the traditional "controlled living radical polymerization" process, the polymer chains formation is initiated at the same time in the bulk of the polymer batch, therefore produce uniform polymer chain length. When applied to polymer aerogel fabrication, this provides a narrower pore distribution, enabling polymer aerogels with low haze.

In a typical process a clear substantially transparent porous aerogel substrate is fabricated by the polymerization of a mixture comprising a suitable solvent, reactive monomers, crosslinkers and control agents to produce a gel. In a second step, the unreacted monomers and initial solvent are removed from the gel by exchange with a different solvent. Finally, the cleaning solvent is removed by controlled slow evaporation or by supercritical $CO_2$ extraction. The polymerization process is generally carried out in a deoxygenated environment for 1 min to 72 hrs at temperatures ranging from 50-150° C. In some cases, photoinitiaton may also be used, at temperatures that can be as low as room temperature.

Suitable monomers include vinyl, acrylate, and methacrylate monomers. Examples of suitable acrylates and methacrylates include (a) monofunctional acrylates and methacrylates such as methyl acrylate, ethyl acrylate, methyl methacrylate, ethyl methacrylate, benzyl methacrylate, lauryl methacrylate, isobornyl methacrylate (b) difunctional acrylates and methacrylates such as 1,3-Butanediol diacrylate, 1,6-hexanediol diacrylate, bisphenol A ethoxylate diacrylate, ethylene glycol diacrylate, poly(ethylene glycol) diacrylate. Suitable vinyl monomers include styrene, divinylbenzene and liquid ethylene derivatives such as, vinyl stearate, vinyl laurate, vinyl benzoate, vinyl acetate, ethyl vinyl ether, vinyl chloride, 1-vinyl-2-pyrrolidone.

Cross-linkers include tri, tetra, penta or hexa-acrylates and methacrylates such as trimethylolpropane triacrylate, trimethylolpropane ethoxylate triacrylate, di(trimethylolpropane) tetraacrylate, dipentaerythritol penta-/hexa-acrylate and the like; 1,3,5-trimethacryloyloxy adamantane, dipenterithritol pentacrylate, trimethylolpropane trimethacrylate, and polyoligosilsequioxane-octamethacrylate.

The colorimetric test strip and the testing device are designed to work with liquid body fluids such as saliva. Therefore, chemical bonding of the sensing chemicals onto the structure of the porous substrate is essential for preventing leaching of the sensing chemicals during penetration of the liquid sample through the pores of the sensing test spots. When grafting method is used for attaching the sensing chemicals, at least one of the monomers or crosslinkers used during gel formation should have functional groups that can bond with the appropriate functional groups from the sensing chemicals. Polymer porous aerogels can incorporate reactive bonding groups including hydroxyl groups (—OH), carboxyl (—COOH), sulfonic acid (—$SO_3H$), amino groups (—$NH_2$, —NHR) and others, from the polymer precursors used for fabrication of the polymer aerogel. In this approach, the bonding groups are generally present onto the monomers or crosslinkers used for the gel formation steps.

Examples of suitable monomers incorporating hydroxyl groups include 2-hydroxyethyl acrylate, glycerol monomethacrylate, hydroxypropyl methacrylate, N-(2-hydroxypropyl)methacrylamide and the like. Examples of monomers or crosslinkers incorporating carboxylic acid groups include acrylic acid, methacrylic acid, 3-butene-1,2,3-tricarboxylic; β-carboxyethyl acrylate, methacryloyl-L-lysine, 4-vinylbenzoic acid, and the like. Examples of monomers incorporating sulfonic acid groups include vinylsulfonic acid, 2-acrylamido-2-methylpropane sulfonic acid, styrenesulfonic acid, and the like. Examples of monomers incorporating amino groups include 2-aminoethyl methacrylate, 2-(tert-butylamino)ethyl methacrylate, N-(3-aminopropyl)methacrylamide; diallylamine, 4-vinylaniline, 2-vinylaniline and the like.

Liquid body fluids such as saliva contain substantial amount of water and water miscible molecules. The test fluid sample should penetrate quickly through the pores of the test strip spots. To facilitate this, the polymer materials of the porous substrate should have a sufficient degree of compatibility with the tested fluid. In the present invention, at least one of the monomers or cross-linking polymer materials are selected such as to be water compatible or miscible. Suitable water miscible monomers include: acryl amide, acrylic acid, methacrylic acid, 2-hydroxyethyl acrylate, glycerol monomethacrylate, polyethyleneglycoldiacrylate, polyethyleneglycoldimethacrylate, vinyl pyrrolidone, and the like.

Generally, the reaction is performed in a solvent which acts as a template to create the solvent-filled voids in the gel structure during polymerization, that become pores after solvent removal. Suitable solvents provide good solubility to the reactive monomers. Particularly suitable are polar aprotic organic solvents such as dimethylformamide, methyl ethyl ketone, toluene, tetrahydrofuran, diethyl ether, diglyme (diethylene glycol dimethyl ether), 1,2-dimethoxyethane, ethyl acetate, xylene and others. Also suitable are high boiling solvents such as acetophenone or n-methylpyrrolidone.

Suitable radical initiators include thermal initiators—activated by heat—and photoinitiators which are activated by light, typically ultra violet in a range of about 200 nm to 400 nm wavelength. Non-limiting examples of thermal initiators includes (a) peroxides such as benzoyl peroxide, diacetylperoxide, di t-butylperoxide, cumyl peroxide; or azo compounds such as AIBN and phenylazotriphenylmethane. Non-limiting examples of photoinitiators include benzophenone, diethoxyacetophenone, benzoylcyclohexanol, Hydroxydimethylacetophenone, benzoin and the like.

The control agent enables formation of small pores and with uniform size distribution, which are key requirements to fabrication of a transparent polymer aerogels. The control agent is selected as a function of the mode of controlling the chain growth in the radical polymerization process. U.S. Pat. No. 10,421,253 describes an example of successful fabrication of substantially transparent polymer aerogels by a process called stable free radical polymerization (SFRP). In this process, the control agent comprises one of: a stable nitroxide, an alkoxyamine, a stable nitroxide derived from decomposition of an alkoxyamine, 2,2,6,6-Tetramethyl-1-piperidinyloxy (TEMPO), or 4-hydroxy-TEMPO.

Another suitable controlled living radical polymetrization is the reversible addition-fragmentation chain transfer (RAFT). For a RAFT process, the control agent may comprise: trithiocarbonates, xanthates, or benzodithioates. Another suitable controlled living polymerization is atom transfer radical polymerization (ATRP). For an ATRP process, the control agent may comprise a transition metal redox center complexed with ligands such as amine-functional ligands. In a different approach, US Patent Application 20190135984 disclosed fabrication of substantially transparent polymer aerogels by using a chain transfer agent, such as molecules containing halogen or thiol groups. Examples of suitable chain transfer agents include an organic thiol chain transfer agent, dodecanethiol, chloroform, octyl mercaptan, or 1,8-dimercapto-3,6-dioxaoctane.

Sensing chemicals are selected such as to have a preference for reacting with a specific target drug of interest. Many detecting chemistries have been developed for solution testing in the laboratory (Clarke's Analysis of Drugs and Poisons in pharmaceuticals, body fluids and postmortem material, Anthony C Moffat M David Osselton Brian Widdop, Jo Watts, FOURTH EDITION, Pharmaceutical Press 2011).

As an example, the detection of the Δ9-tetrahydrocannabinol (THC), present in smoked cannabis or in vaping THC oils, detection is generally performed in solutions by mixing and shaking the test sample with a solution containing either Fast Blue B salt or with Fast Blue BB salts, which change color in the presence of THC (see Chemical Formula 1).

Formula 1: Dyes used to detect THC in solution.

Fast Blue B Salt

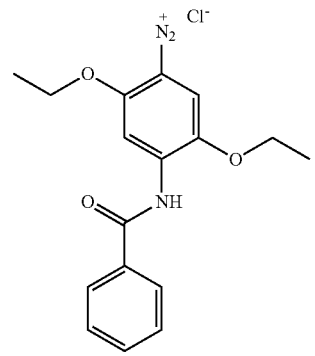

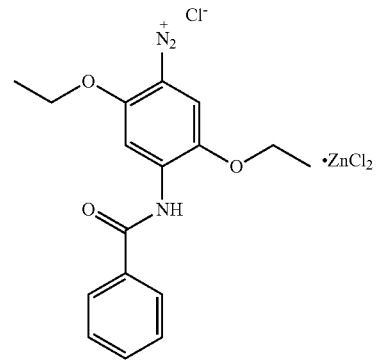

Fast Blue BB Salt

The detection mechanism of THC is based on the formation of the compound 1 in Formula 2, which has an increased absorption in the 500 nm to 600 nm region of the visible spectrum, which is not present in the absorption spectrum of the sensing chemicals before reaction.

Formula 2. Detection reaction of THC with Fast Blue B salt

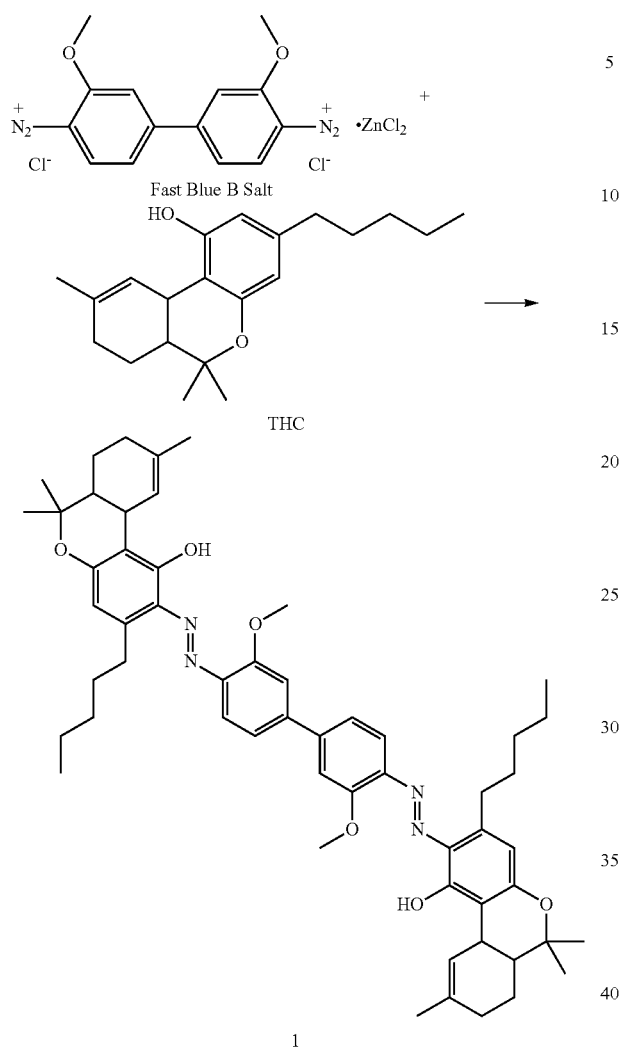

One method of incorporation would involve infusing the aerogel (silica or polymer) with the sensing chemicals from a solution, followed by slow solvent evaporation. Infusion has been used to infuse paper substrates with sensing dyes (G. Musile et al., Anal. Methods, 2015, 7, 8025-8033). However, this method would produce a sensor where the sensing chemicals are loosely dispersed within the pores of the aerogel. During testing of liquid samples, the loosely dispersed dyes are displaced out of the porous substrate during the advancement of the tested fluid. This can result in test spots with poor and non-uniform coloration and with little reproducibility, since most of the sensing chemicals are moved to the edges of the test spots and as such, they lost for the purpose of detection.

Embodiments described below can provide more robustly attached sensing chemicals onto the porous substrate. In one embodiment, the sensing chemical is incorporated as is, into the aerogel by placing a suitable amount of the sensing dye (such as Fast Blue B Salt when testing for THC) in the solution at the moment of fabrication of the gel from precursors. This applies both to sol-gels involved in fabrication of silica aerogels and to the polymer gels when fabricating polymer aerogel sensing test strips. Upon solvent exchange, the loose sensing chemical is removed, but a certain amount of sensing chemical is embedded and therefore immobilized into the walls of the pores from the porous support. While the attachment to the support is relatively weak, this may be in some cases sufficient for the purpose of fast drug testing, since the test spot should be stable for up to 3 minutes altogether.

Figure 3:
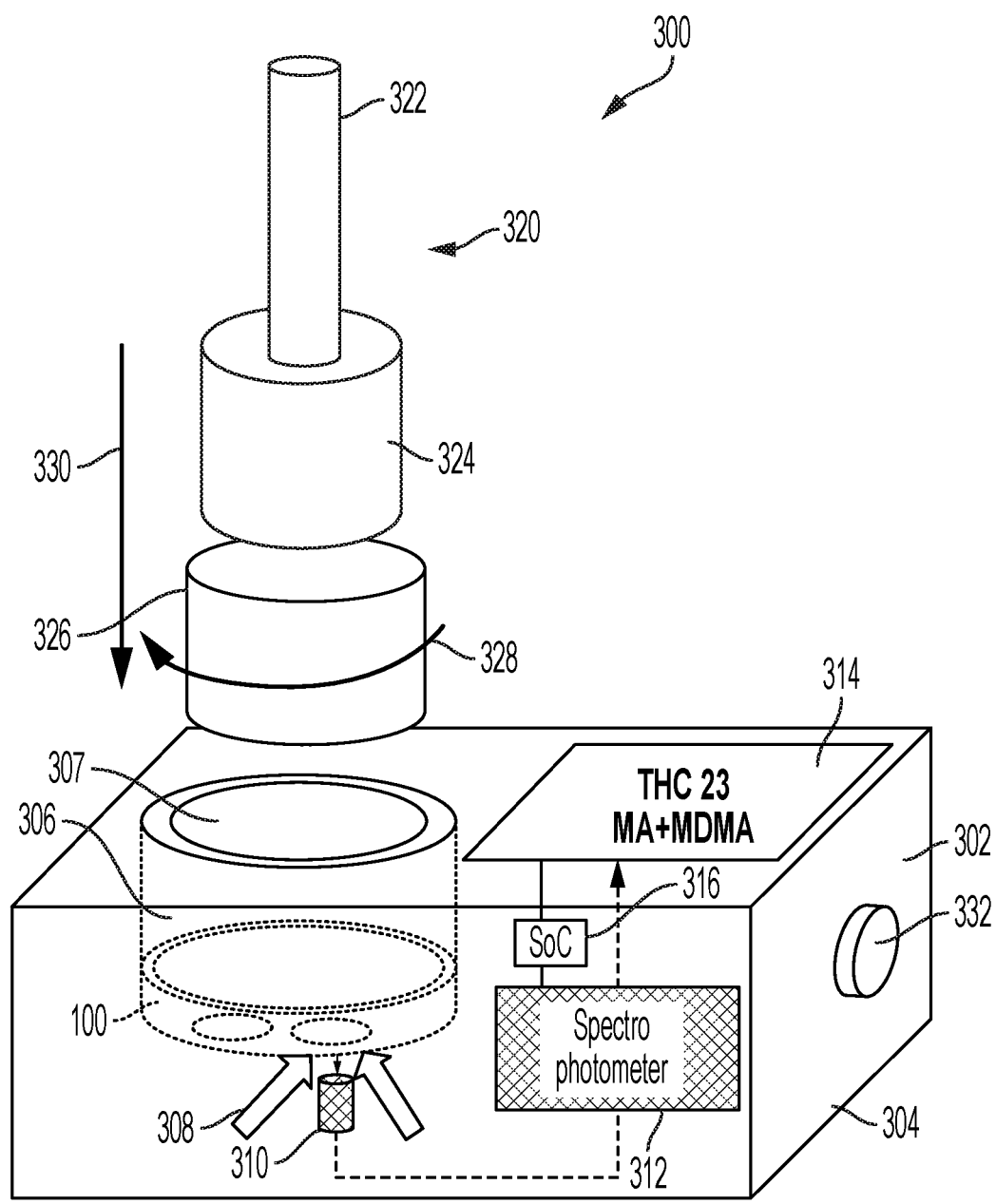
FIG. 3 is a perspective view of a drug testing system according to an example embodiment.

In another embodiment, the sensing chemical modified chemically to be provided with chemical functional groups that can bond onto the walls of the pores of the porous support by a chemical reaction with the functional groups present onto the structure of the porous substrate. As a representative example, FIG. 3 shows examples of suitably modified Fast Blue B and Fast Blue BB salts to enable chemical bonding onto the porous substrate.

Formula 3. Chemically modified sensing chemicals, derived from Fast Blue B salt, for chemical bonding onto the porous support

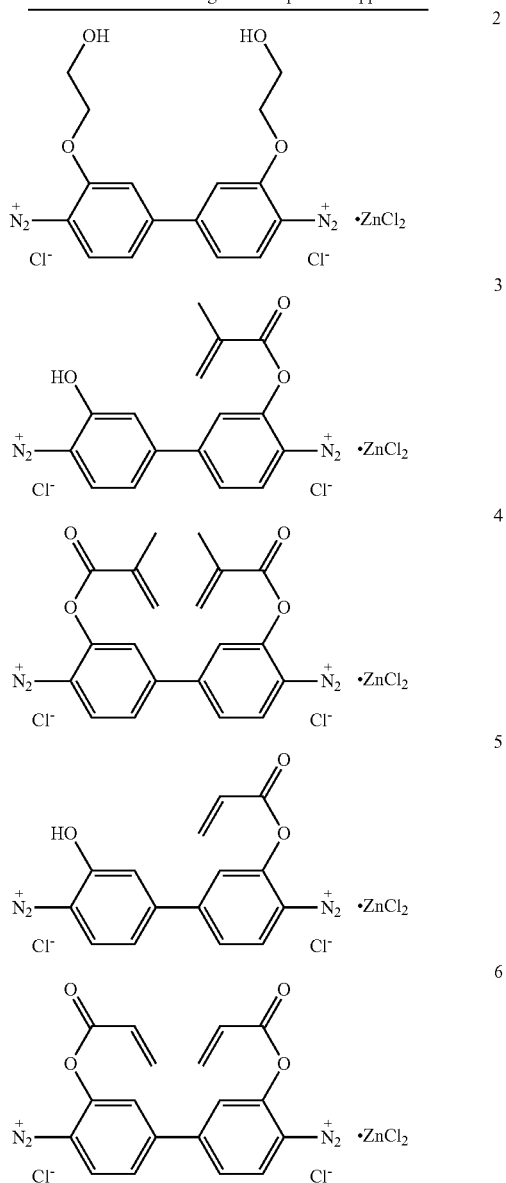

The process for chemical bonding of the sensing chemical onto the porous support materials is dependent on the chemical functions present onto the sensing chemicals. As an example, the modified Fast Blue B salt, compound 2 possessing hydroxyl (—OH) reactive groups, is preferably chemically bonded by reacting it from a solution of this compound soaking a pre-made aerogel (silica or polymer) with suitablefunctional groups. Chemical bonding is achieved for example when the hydroxyl (—OH) on compound 2 is reacted with a porous support material containing carboxylic acid groups to form carboxylic acid esters or with a sulfonic acid to form sulfonic acid esters. Various other functional groups may be introduced such as those that are compatible to react with the functional groups from the porous support. Suitable reactive functional groups include: hydroxyl (—OH); amine (—NH2; —NHR), carboxylic and sulfonic acid groups, and the like. For example, the bonding can be achieved through the formation of an amide, imide, urethane, carbonate bonding when appropriate functional groups are used onto the sensing chemicals and the porous substrate.

Figure 4:
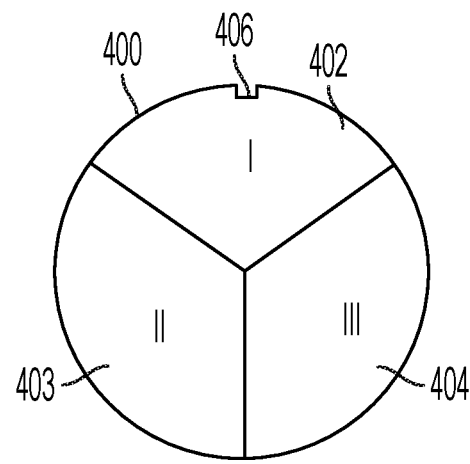
FIG. 4 is a diagram of a multiple drug test strip according to an example embodiment.

Another functional group suitable for bonding is the carbon-carbon double bond, for example from vinyl, acrylate or methacrylate polymerizable functional groups (see Formula 3, compounds 3-6). In this approach, the modified sensing chemical containing the polymerizable group is introduced into the gel formulation as one of the monomers, at the time of the fabrication of the gel. Completion of the general steps for aerogel formation produces a gel with the sensing chemical incorporated into the polymer structure, which does not leach or move in the presence of liquids such as test liquid samples. The same method is suitable with Fast Blue BB Salt. Examples of vinyl, acrylate and metyhacrylate functionalized Fast Blue BB salt are shown in FIG. 4.

Formula 4. Vinyl, acrylate and methacrylate derivatives of Fast Blue BB suitable for direct polymerization with monomers and cross-linkers.

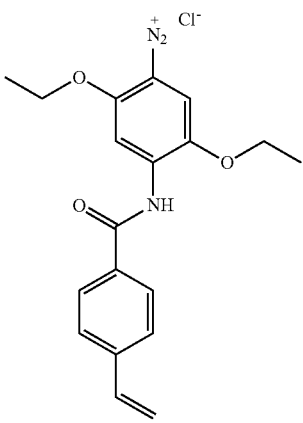

7

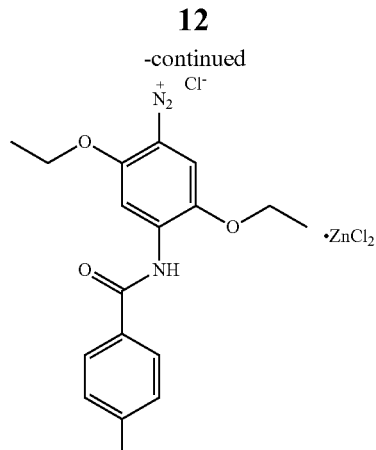

8

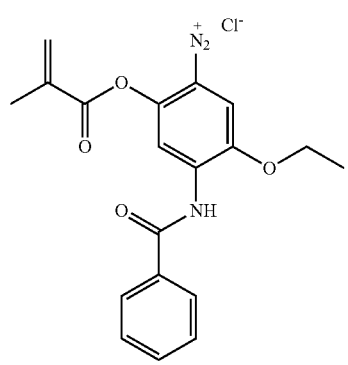

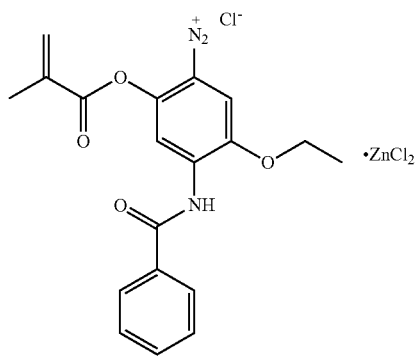

9

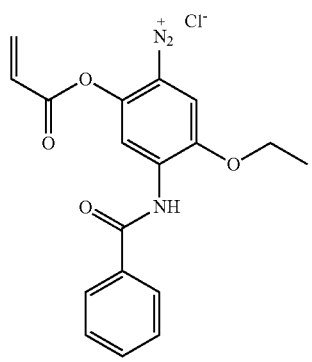

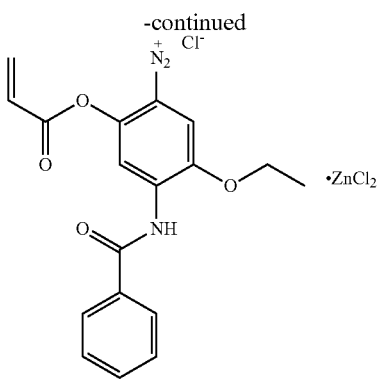

With respect to specific example of detection of THC with Fast Blue Salts, the sensing species is the diazonium salt. The diazonium salt can be present onto the Fast Blue salt at the time of its incorporation onto the gel as described above. Another suitable approach involves first chemically bonding a primary amino precursor of the Fast Blue salts onto the porous support and performing the diazotation reaction in the next step. As an example, the diazonium salt and its corresponding amino precursor that may be used for this approach are shown for Fast Blue BB salt in Formula 5.

Formula 5. Diazonium salt and amino precursor suitable for incorporation into aerogel test spot.

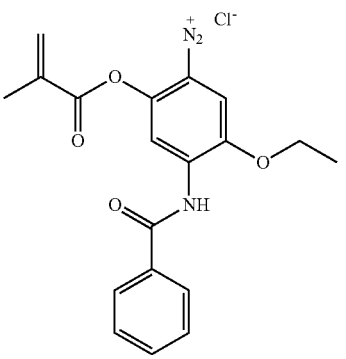

Polymerizable Fast Blue BB Diazonium Salt

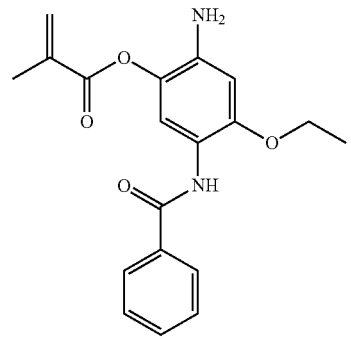

Polymerizable Fast Blue BB Amino precurson

Figure 2:
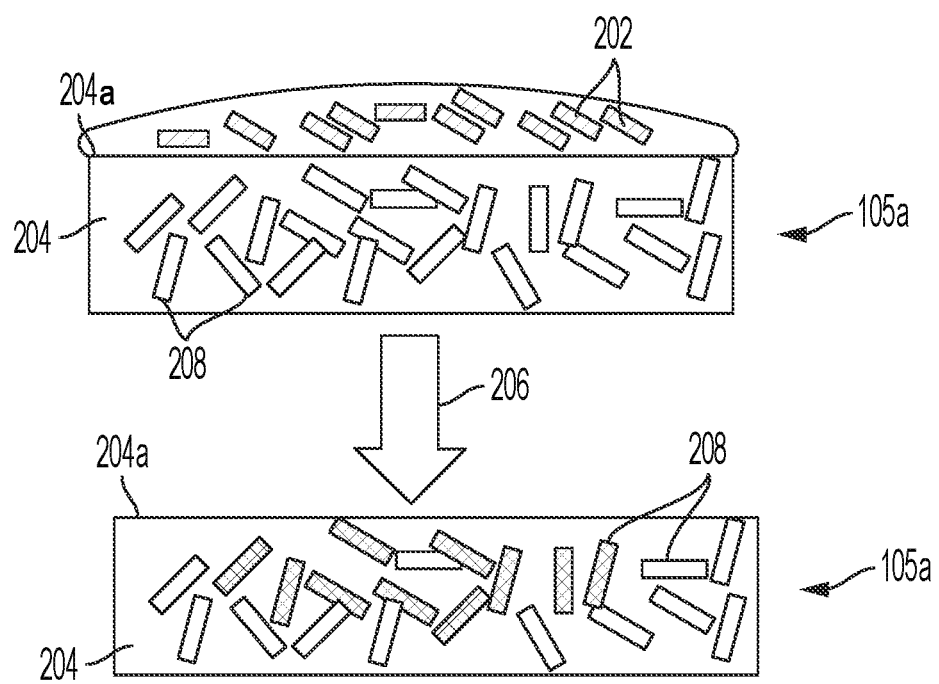
FIG. 2 is a diagram showing drug detection using a test strip according to example embodiments.

In FIG. 2, a diagram shows a section of the porous support material incorporating sensing chemicals, 105a. In the top of the figure, a sample of fluid 200 (e.g., saliva) is placed on the top surface 204a of the porous support material 204. The sample 200 has a concentrated amount of a drug 202 that is subject to testing. As indicated by the arrow 206, the sample fluid 200 is absorbed into the support material 204 where it contacts at least one of the sensing chemicals 208. As indicated by the shaded sensing chemicals 208, the chemical reacts with the drug 202 and undergoes a color change. The amount of the color change is indicative of a concentration of the drug 202 in the test fluid 200.

Generally, at least part of the enclosure 101 may be transparent, facilitating colorimetric sensing via an externally located optical device, e.g., light source and light detector. The optical device can accurately measure a change in color of the sensing chemicals 208, such that a concentration of drugs in the test fluid that is above a threshold level can be determined based on a corresponding change in color.

In FIG. 3, a perspective view shows a testing system 300 according to an example embodiment. The system 300 includes a test apparatus 302 that houses mechanical and electrical components of the system 300, such as an enclosure 304 and power supply (not shown). The enclosure 304 includes a test chamber 306 (e.g., cavity) joined to a guiding channel 307 into which a test strip 100 is inserted. At the bottom of the cavity 306 is a light source 308 (e.g., laser, light emitting diode) that illuminates the test strip 100. A photodetector 310 detects emissions of the light 308 from the test strip 100 and sends a signal to a photometer 312.

The photometer 312 includes a detection circuit that can determine spectral properties as a function of wavelength. In some embodiments, absorptance as a function of wavelength is used. Based on the detected optical properties, drug concentrations above a threshold may be detected. If drugs are detected, a display 314 provides an indication. The display 314 may include any combination of indicator lights, numeric display, alphanumeric display, etc. Other indicator device may be used instead of or together with the display 314, e.g., an analog or digital meter, speaker driven by a speech synthesizer or tone generator, etc. Generally, the light source 308, sensor 310 photometer 312, and display 314 may all be coupled to computing hardware, indicated here as a system on a chip (SoC) 316. The SoC 316 may include processors, volatile and non-volatile memory, input/output circuitry, and specialized circuitry such as analog-to-digital converters, digital-to-analog converters, power management circuits, etc.

For ease of testing, the system 300 may utilize a swab 320 that includes a handle 322 and collection sponge 324. The swab 322 can be fixably attached to a sleeve 326, e.g., via a twist lock action as indicated by arrow 328. Other attachment mechanisms between the swab 320 and sleeve 326 may be used, such as snap lock, adhesive, etc. After attachment of the swab 320 to the sleeve 326, the assembly is inserted into the test chamber 306 as indicated by arrow 330 to perform testing.

Once sufficient force is placed on the handle 322 in the direction of the arrow, the sponge 324 will contact the test strip 100. A sensor (e.g., switch) may be used that determines the exact moment contact occurs, allowing for a first optical reading just before or after contact occurs. In other embodiments, the test strip 100 may be placed into the test chamber 306 together with the swab 320, e.g., attached with or integrated with the sleeve. In such a case, the test strip 100 or sleeve 324 may have a breakaway feature that prevents contact between the sponge 324 and the test strip 100 until sufficient pressure is exerted on the handle 322.

After contact of the swab sponge 324 with the test strip 100, the testing may be initiated by a user input, e.g., button 332. In other embodiments, the test may be initiated automatically just before or after contact occurs between the sponge 324 and test strip 100, e.g., via a microswitch or pressure sensor in the test chamber 306 that detects the contact. After testing, the test strip 100 and swab 302 are withdrawn (either together or separately) from the apparatus 302 and may be saved (e.g., for evidence) or disposed of as appropriate.

Generally, the SoC 316 is configured to illuminating a colorimetric test spot within the test strip 100, and detecting a wavelength emitted therefrom. This is used to obtain a first baseline reading before or after the contact between the swab 320 and the test strip 100 and a second reading after a predetermined elapsed time after the contact. Based on a difference signal between the first and second readings, the SoC 316 determines a numeric value for a concentration of a drug that is correlated with the intensity of the difference signal. An indication of the numeric value is provided via the test apparatus 302, e.g., via display 314.

Note that the embodiments described above allow for multiple drug tests to be performed using the same test strip. In some embodiments, if the different sensing chemicals have sufficiently different optical properties (e.g., absorption center wavelength), then the different chemical sensors may be evenly dispersed through the test strip, and detection of one or more chemicals is based on peaks at different wavelengths. In one embodiment, two or more colorimetric test spots can be illuminated simultaneously. Two or more respective detected individual wavelengths emitted by the two or more colorimetric test spots can be used to provide respective two or more numeric values. In another embodiment, two or more colorimetric test spots that are illuminated with two or more different light sources such that two or more respective detected wavelengths are different for each colorimetric test spot. In another embodiment, two or more colorimetric test spots that are illuminated in succession, and the detected wavelengths emitted are measured successively.

In other embodiments, the test strip may have different regions that utilize different sensing chemicals. An example of this is shown in FIG. 4, in which a test strip 400 according to an example embodiment has three difference zones 402-404 that have different sensing chemicals I-III. A testing apparatus may use multiple light sources and/or detectors to test each zone 402-404 individually or at the same time. Also note that the test strip includes an alignment feature (e.g., notch 406) that ensures all test strips are inserted into the tester at the same orientation such that the different zones 402-404 will be aligned with the correct light sources and/or detectors.

In Table 2 below, various performance characteristics of the currently disclosed test strips are compared to that of commercially-available immunoassays. In this table, the term "test strip" refers to the disclosed test strip (e.g., strip 100 in FIG. 1) and "test device" refers to disclosed test apparatus (e.g., apparatus 302 in FIG. 3).

TABLE 2

| Performance characteristics | Commercial Immunoassays | Colorimetric Test Strip |
| --- | --- | --- |
| Test duration | 3 min | <1 min |
| Cost per test | $24 | <$12 |
| Temperature range | 5° C.-40° C. (testing) 5° C.-25° C. (test kit storage) | 0°-40° C. (testing) −20° C.-70° C. (test strip storage) |

TABLE 2-continued

| Performance characteristics | Commercial Immunoassays | Colorimetric Test Strip |
| --- | --- | --- |
| Minimum detection levels | 25 ng/mL | 25 ng/mL |

Figure 5:
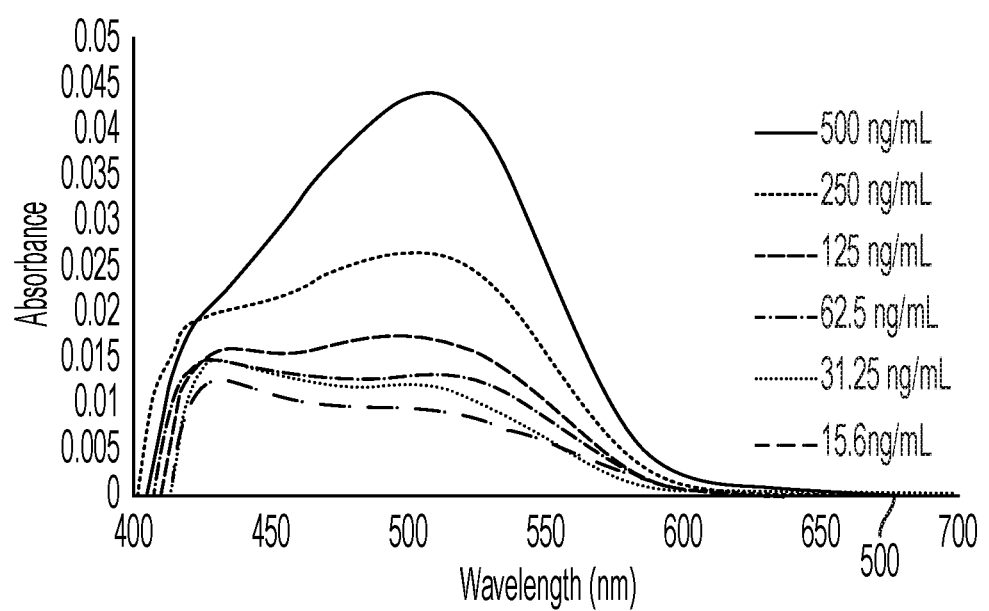
FIG. 5 is a diagram showing experimental results of a test with a solution of containing a dissolved sensing chemical.

Preliminary experiments were undertaken to test the spectroscopic detection of THC in very low concentrations solutions. Results of the test are shown in FIG. 5. For increased accuracy, the reported absorbance signal in graph 500 is baseline corrected. This involves subtracting a baseline from the measured signal for each individual measurement. These measurements were performed with calibrated solutions of THC at various concentrations. The height of the absorbance signal in the graph 500 is associated with the concentration of the THC in the tested solution. It was encouraging to find out that THC could be detected at concentrations that are relevant to police target of 25 ng/mL.

The second preliminary tests looked at the speed of the detection of THC within the samples. Measurement of the baseline corrected absorbance curves shown in FIG. 5 were successfully completed within a solution giving a fastest time with the setup of 28 seconds. Further proving the capability of the technology is the strength of the signal at 28 seconds.

Figure 6:
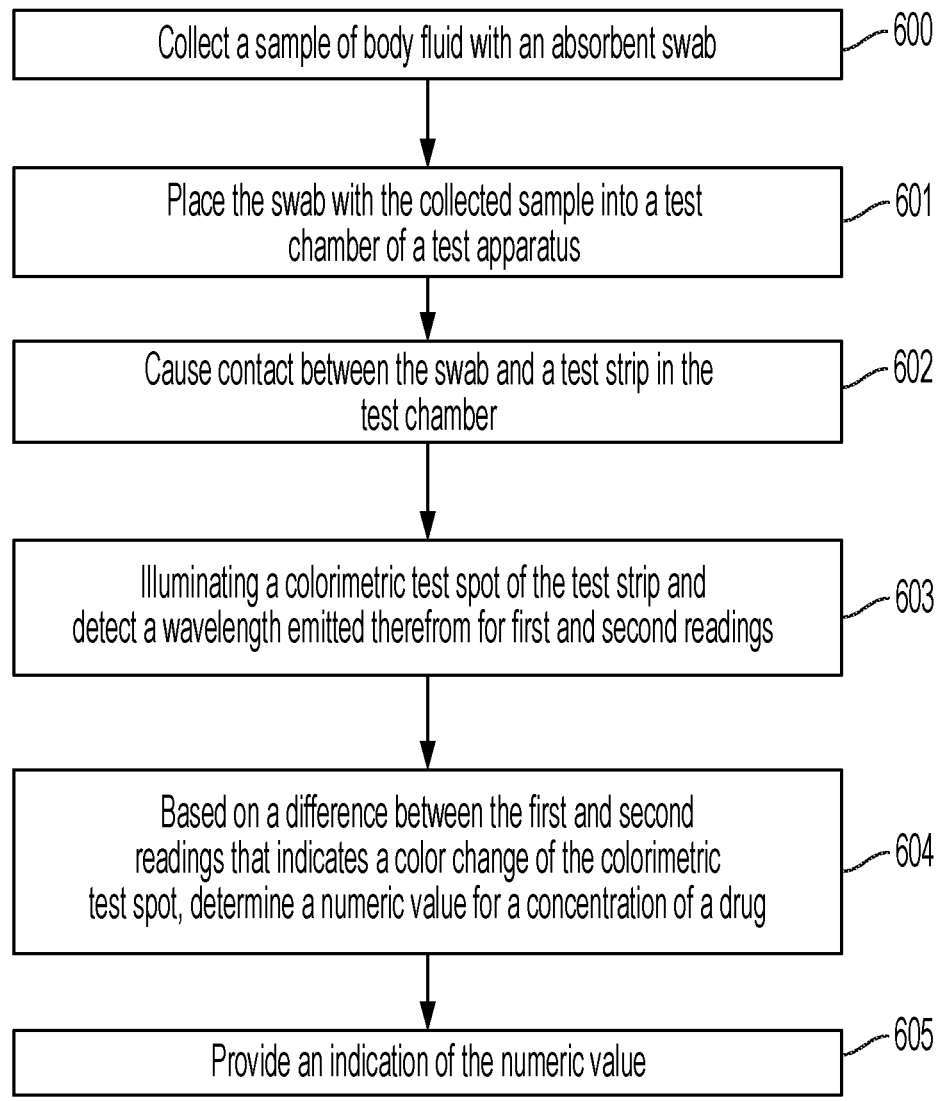
FIG. 6 is a flowchart of a method according to an example embodiment.

In FIG. 6, a flowchart shows a method according to an example embodiment. The method involves collecting 600 a sample of body fluid with an absorbent swab. The swab and collected sample are placed 601 into a test chamber of a test apparatus. Contact is caused 602 between the swab and a test strip in the test chamber. The test strip has one or more colorimetric test spots comprising sensing chemicals embedded within a porous support material. The colorimetric test spots are illuminated, and a wavelength emitted therefrom is detected 603 for first and second readings. The first reading occurs just before or after the contact between the swab and the test strip and the second reading occurs a predetermined time after the contact. Based on a difference between the first and second readings that indicates a color change of the colorimetric test spot, a numeric value for a concentration of a drug that is correlated with the color change is determined 604. An indication of the numeric value is provided 605 via the test apparatus.

Embodiments of the present invention include the following items:

Item 1. A test strip comprising a substantially transparent substrate; and one or more colorimetric test spots on the transparent substrate, each colorimetric test spot comprising one or more sensing chemicals chemically attached onto a porous support material, wherein the porous support material has at least one exposed surface configured to absorb a body fluid, the one or more sensing chemicals configured to change a color in response to a presence of a target drug in the body fluid.

Item 2. The test strip of Item 1, wherein the substrate is made of the porous support material and the colorimetric test spots are embedded within the substrate.

Item 3. The test strip of Items 1 or 2, further comprising an enclosure that partly encompasses the colorimetric test spots, wherein at least part of the enclosure and porous support material are transparent at a wavelength corresponding to the color.

Item 3A. The test strip of Items 1 or 2, wherein the porous support material is transparent at a wavelength range from 360 nm to 800 nm.

Item 4. The test strip of any of Items 1-3A, wherein the porous support material comprises an aerogel formed of inorganic silica or a polymer.

Item 5. The test strip of any of Items 1-4, wherein at least one of monomers and cross-linkers used for fabrication of the porous support material is hydrophilic.

Item 6. The test strip of any of Items 1-5, wherein the pores of the support porous material have an average size smaller than 20 nm.

Item 7. The test strip of and of Items 1-6, wherein at least one of monomers and cross-linkers used for fabrication of the support material is selected from a group consisting of 2-hydroxyethyl acrylate, glycerol monomethacrylate, hydroxypropyl methacrylate, N-(2-hydroxypropyl)methacrylamide; acrylic acid, methacrylic acid, 3-butene-1,2,3-tricarboxylic; β-carboxyethyl acrylate, methacryloyl-L-lysine, 4-vinylbenzoic acid; vinylsulfonic acid, 2-acrylamido-2-methylpropane sulfonic acid, styrenesulfonic acid; 2-aminoethyl methacrylate, 2-(tert-butylamino)ethyl methacrylate, N-(3-aminopropyl)methacrylamide; diallylamine, 4-vinylaniline, 2-vinylaniline; acryl amide, acrylic acid, methacrylic acid, 2-hydroxyethyl acrylate, glycerol monomethacrylate, polyethyleneglycoldiacrylate, polyethyleneglycoldimethacrylate, vinyl pyrrolidone.

Item 8. The test strip of any of Items 1-7, wherein the one or more colorimetric test spots comprise a multitude of particles embedded within the porous support material, the particles incorporating the one or more sensing chemicals.

Item 9. The test strip of any of Items 1-7, wherein the one or more colorimetric test spots comprise a block embedded within the porous support material, the block incorporating the one or more sensing chemicals.

Item 10. The test strip of any of Items 1-9, wherein the color change indicates detection of one or more of amphetamines, parent amphetamine molecules, methamphetamine (MA), methylenedioxymethamphetamine (MDMA), cocaine or Δ9-tetrahydrocannabinol (THC).

Item 11. A method comprising: collecting a sample of body fluid with an absorbent swab; placing the swab with the collected sample into a test chamber of a test apparatus; causing contact between the swab and a test strip in the test chamber, the test strip comprising one or more colorimetric test spots that are placed onto a transparent substrate or are embedded within a porous support material; illuminating the colorimetric test spots and detecting a wavelength emitted therefrom for first and second readings, the first reading occurring just before or after the contact between the swab and the test strip and the second reading occurring a predetermined time after the contact; based on a difference between the first and second readings that indicates a color change of the colorimetric test spot, determining a numeric value for a concentration of a drug that is correlated with the color change; and provide an indication of the numeric value via the test apparatus.

Item 12. The method of Item 11, wherein the one or more colorimetric test spots comprise two or more colorimetric test spots that are illuminated simultaneously, wherein two or more respective detected individual wavelengths emitted by the two or more colorimetric test spots provide respective two or more numeric values.

Item 13. The method of Items 11 or 12, wherein the one or more colorimetric test spots comprise two or more colorimetric test spots that are illuminated with two or more different light sources such that two or more respective detected wavelengths are different for each colorimetric test spot.

Item 14. The method of Item 11 or 12, wherein the one or more colorimetric test spots comprise two or more colorimetric test spots that are illuminated in succession, and the detected wavelengths emitted are measured successively.

Item 15. The method of any of Items 11-14, wherein the difference signal senses a parent molecule of the drug.

Item 16. The method of any of Items 11-15, wherein the body fluid comprises at least one of blood, urine, plasma, and saliva.

Item 17. The method of any of Items 11-16, wherein an elapsed time between the contact and the providing of the indication is less than 5 minutes.

Item 18. The method of any of Items 11-17, wherein the color change indicates detection of one or more of amphetamines, parent amphetamine molecules, methamphetamine (MA), methylenedioxymethamphetamine (MDMA), cocaine or Δ9-tetrahydrocannabinol (THC).

Item 19. A system comprising: a test strip comprising one or more colorimetric test spots each comprising one or more sensing chemicals chemically attached onto a porous support; a swab operable to collect a sample of body fluid; a test apparatus comprising: a test chamber comprising an optical reader and configured to receive the test strip and at least part of the swab; an indicator device; and a processor coupled to the optical reader and the indicator device and configured to perform: detecting a wavelength of light emitted from the colorimetric test spot for first and second readings, the first reading occurring just before or after the contact between the swab and the test strip and the second reading occurring a predetermined time after the contact; based on a difference between the first and second readings that indicates a color change of the colorimetric test spot, determining a numeric value for a concentration of a drug that is correlated with the color change; and providing an indication of the numeric value via the indicator device.

Item 20. The system of Item 19, wherein the test strip comprises substrate onto which the colorimetric test spots are placed, and wherein the porous support material has at least one exposed surface configured to absorb a body fluid, the one or more sensing chemicals configured to change a color in response to a presence of a target drug in the body fluid, wherein the substrate and the porous support material are substantially transparent at a wavelength corresponding to the color.

Item 21. The system of Items 19 or 20, wherein the difference signal senses a parent molecule of the drug.

Item 22. The system of any of Items 19-21, wherein the body fluid comprises at least one of blood, urine, plasma, and saliva.

Item 23. The system of any of Items 19-22, wherein an elapsed time between the contact and the providing of the indication is less than 5 minutes.

Item 24. The system of any of Items 19-23, wherein the color change indicates detection of one or more of amphetamines, parent amphetamine molecules, methamphetamine (MA), methylenedioxymethamphetamine (MDMA), cocaine or Δ9-tetrahydrocannabinol (THC).

Item 25. The system of any of Items 19-24, wherein the one or more colorimetric test spots comprises a multitude of particles embedded within the porous support material, the particles incorporating the one or more sensing chemicals.

Item 26. The system of any of Items 19-24, wherein the one or more colorimetric test spots comprises a block embedded within the porous support material, the block incorporating the one or more sensing chemicals.

Item 27. The system of Items 19-26, wherein the porous support material comprises an aerogel formed of inorganic silica or a polymer.

Item 28. The system of Items 19-27, wherein the wavelengths of the first and second readings are detected through the transparent substrate.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g. 1 to 5 includes 1, 1.5, 2, 2.75, 3, 3.80, 4, and 5) and any range within that range.

The foregoing description of the example embodiments has been presented for the purposes of illustration and description. It is not intended to be exhaustive or to limit the embodiments to the precise form disclosed. Many modifications and variations are possible in light of the above teaching. Any or all features of the disclosed embodiments can be applied individually or in any combination are not meant to be limiting, but purely illustrative. It is intended that the scope of the invention be limited not with this detailed description, but rather determined by the claims appended hereto.

The invention claimed is:

1. A test strip comprising:
a substantially transparent substrate; and
one or more colorimetric test spots on the transparent substrate, each colorimetric test spot comprising one or more sensing chemicals chemically attached onto a porous support material, wherein the porous support material has at least one exposed surface configured to absorb a body fluid, the one or more sensing chemicals configured to change a color in response to a presence of a target drug in the body fluid,
wherein the one or more colorimetric test spots on the transparent substrate are surrounded by the transparent substrate without the one or more sensing chemicals, and wherein the body fluid contacts the exposed surface.

2. The test strip of claim 1, wherein the substrate is made of the porous support material and the colorimetric test spots are embedded within the substrate.

3. The test strip of claim 1, wherein the porous support material is substantially transparent at a wavelength of light illuminating the test strip, the wavelength corresponding to the color.

4. The test strip of claim 1, wherein the porous support material comprises an aerogel formed of inorganic silica or a polymer.

5. The test strip of claim 4, wherein at least one of monomers and cross-linkers used for fabrication of the porous support material is hydrophilic.

6. The test strip of claim 4 wherein pores of the porous support material have an average size smaller than 20 nm.

7. The test strip of claim 4, wherein at least one of monomers and cross-linkers used for fabrication of the porous support material is selected from a group consisting of 2-hydroxyethyl acrylate, glycerol monomethacrylate, hydroxypropyl methacrylate, N-(2-hydroxypropyl)methacrylamide; acrylic acid, methacrylic acid, 3-butene-1,2,3-tricarboxylic; β-carboxyethyl acrylate, methacryloyl-L-lysine, 4-vinylbenzoic acid; vinylsulfonic acid, 2-acrylamido-2-methylpropane sulfonic acid, styrenesulfonic acid; 2-aminoethyl methacrylate, 2-(tert-butylamino)ethyl methacrylate, N-(3-aminopropyl)methacrylamide; diallylamine, 4-vinylaniline, 2-vinylaniline; acryl amide, acrylic acid, methacrylic acid, 2-hydroxyethyl acrylate, glycerol monomethacrylate, polyethyleneglycoldiacrylate, polyethyleneglycoldimethacrylate, and vinyl pyrrolidone.

8. The test strip of claim 1, wherein the one or more colorimetric test spots comprise a multitude of particles embedded within the porous support material, the particles incorporating the one or more sensing chemicals.

9. The test strip of claim 1, wherein the one or more colorimetric test spots comprise a block embedded within the porous support material, the block incorporating the one or more sensing chemicals.

10. The test strip of claim 1, wherein the color change indicates detection of one or more of amphetamines, parent amphetamine molecules, methamphetamine(MA), methylenedioxymethamphetamine (MDMA), cocaine and Δ9-tetrahydrocannabinol (THC).

11. A method comprising:
collecting a sample of body fluid with an absorbent swab;
placing the swab with the collected sample into a test chamber of a test apparatus;
causing contact between the swab and an exposed surface of a test strip in the test chamber, the test strip comprising one or more colorimetric test spots that are embedded within a porous support material comprising an aerogel, wherein the one or more colorimetric test spots are surrounded by the porous support material without the one or more colorimetric test spots;
illuminating the colorimetric test spots and detecting a wavelength emitted therefrom for first and second readings, the first reading occurring just before or after the contact between the swab and the test strip and the second reading occurring a predetermined time after the contact;
based on a difference between the first and second readings that indicates a color change of the colorimetric test spot, determining a numeric value for a concentration of a drug that is correlated with the color change; and
provide an indication of the numeric value via the test apparatus.

12. The method of claim 11, wherein the one or more colorimetric test spots comprise two or more colorimetric test spots that are illuminated simultaneously, wherein two or more respective detected individual wavelengths emitted by the two or more colorimetric test spots provide respective two or more numeric values.

13. The method of claim 11, wherein the one or more colorimetric test spots comprise two or more colorimetric test spots that are illuminated with two or more different light sources such that two or more respective detected wavelengths are different for each colorimetric test spot.

14. The method of claim 11, wherein the one or more colorimetric test spots comprise two or more colorimetric test spots that are illuminated in succession, and the detected wavelengths emitted are measured successively.

15. The method of claim 11, wherein the difference between the first and second readings senses a parent molecule of the drug.

16. The method of claim 11, wherein the body fluid comprises at least one of blood, urine, plasma, and saliva.

17. The method of claim 11, wherein an elapsed time between the contact and the providing of the indication is less than 5 minutes.

18. The method of claim 11, wherein the color change indicates detection of one or more of amphetamines, parent amphetamine molecules, methamphetamine(MA), methylenedioxymethamphetamine (MDMA), cocaine and Δ9-tetrahydrocannabinol (THC).

19. A system comprising:
- a test strip comprising one or more colorimetric test spots each comprising one or more sensing chemicals chemically attached onto a porous support material comprising an aerogel, wherein the one or more colorimetric test spots are surrounded by the porous support material without the one or more sensing chemicals;
- a swab operable to collect a sample of body fluid;
- a test apparatus comprising:
  - a test chamber comprising an optical reader and configured to receive the test strip and at least part of the swab, wherein the swab contacts an exposed surface of the test strip;
  - an indicator device; and
  - a processor coupled to the optical reader and the indicator device and configured to perform:
    - detecting a wavelength of light emitted from the colorimetric test spot for first and second readings, the first reading occurring just before or after a contact between the swab and the test strip and the second reading occurring a predetermined time after the contact;
    - based on a difference between the first and second readings that indicates a color change of the colorimetric test spot, determining a numeric value for a concentration of a drug that is correlated with the color change; and
    - providing an indication of the numeric value via the indicator device.

20. The system of claim 19, wherein the test strip comprises a substrate onto which the colorimetric test spots are placed, and wherein the porous support material has at least one exposed surface configured to absorb a body fluid, the one or more sensing chemicals configured to change a color in response to a presence of a target drug in the body fluid, wherein the substrate and the porous support material are substantially transparent at a wavelength of light illuminating the test strip, the wavelength corresponding to the color.

21. The system of claim 19, wherein the difference between the first and second readings senses a parent molecule of the drug.

22. The system of claim 19, wherein the body fluid comprises at least one of blood, urine, plasma, and saliva.

23. The system of claim 19, wherein an elapsed time between the contact and the providing of the indication is less than 5 minutes.

24. The system of claim 19, wherein the color change indicates detection of one or more of amphetamines, parent amphetamine molecules, methamphetamine(MA), methylenedioxymethamphetamine (MDMA), cocaine and 49-tetrahydrocannabinol (THC).

25. The system of claim 19, wherein the one or more colorimetric test spots comprises a multitude of particles embedded within the porous support material, the particles incorporating the one or more sensing chemicals.

26. The system of claim 19, wherein the one or more colorimetric test spots comprises a block embedded within the porous support material, the block incorporating the one or more sensing chemicals.

27. The system of claim 19, wherein the aerogel is formed of inorganic silica or a polymer.

28. The system of claim 19, wherein the wavelengths of the first and second readings are detected through the porous support material.

* * * * *